(12) United States Patent
Meyer et al.

(10) Patent No.: US 10,914,737 B2
(45) Date of Patent: Feb. 9, 2021

(54) METHOD FOR AUTOMATED EVALUATION OF INCUBATED IMMUNOBLOT STRIPS

(71) Applicant: EUROIMMUN MEDIZINISCHE LABORDIAGNOSTIKA AG, Luebeck (DE)

(72) Inventors: Wolfgang Meyer, Pansdorf (DE); Thomas Scheper, Berkenthin (DE); Robert Kaffka, Dassow (DE)

(73) Assignee: EUROIMMUN Medizinische Labordiagnostika AG, Luebeck (DE)

( * ) Notice: Subject to any disclaimer, the term of this patent is extended or adjusted under 35 U.S.C. 154(b) by 502 days.

(21) Appl. No.: 14/786,751

(22) PCT Filed: Apr. 4, 2014

(86) PCT No.: PCT/EP2014/056787
§ 371 (c)(1),
(2) Date: Oct. 23, 2015

(87) PCT Pub. No.: WO2014/173657
PCT Pub. Date: Oct. 30, 2014

(65) Prior Publication Data
US 2016/0097724 A1 Apr. 7, 2016

(30) Foreign Application Priority Data

Apr. 24, 2013 (DE) .......... 10 2013 007 045
May 21, 2013 (DE) .......... 10 2013 008 468

(51) Int. Cl.
*G01N 33/543* (2006.01)
*G01N 21/78* (2006.01)
(Continued)

(52) U.S. Cl.
CPC ..... *G01N 33/54386* (2013.01); *G01N 21/253* (2013.01); *G01N 21/78* (2013.01); *G01N 21/8483* (2013.01); *G01N 33/543* (2013.01)

(58) Field of Classification Search
CPC ........................... G01N 33/53–33/577
See application file for complete search history.

(56) References Cited

U.S. PATENT DOCUMENTS 5,270,164 A * 12/1993 Anderson ............ G01N 33/533
435/21
6,847,451 B2 * 1/2005 Pugh .................. G01N 21/8483
356/39

(Continued)

FOREIGN PATENT DOCUMENTS

WO   WO 99/53288 A2   10/1999
WO   WO 2008/144588 A2   11/2008
(Continued)

OTHER PUBLICATIONS

The University of Sydney, "Alpha Innotech Digital Imaging System", 2011, retrieved from http://sydney.edu.au/medicine/bosch/facilities/molecular-biology/digital-imaging/alpha-innotech.php on Mar. 12, 2018, two pages.*

(Continued)

*Primary Examiner* — Christine Foster
(74) *Attorney, Agent, or Firm* — Grüneberg and Myers PLLC

(57) ABSTRACT

The invention relates to a device and a method for automated evaluation of incubated immunoblot strips (5). What is essential for such immunoblot strips (5) is that these have regions coated with antigens, which regions discolour under the formation of so-called bands (6) as soon as a binding occurs, in particular between the antigen and an antibody present in a patient sample. Within the scope of the described technical solution, a camera (2) is initially used to (Continued)

make recordings of the surface of an incubated immunoblot strip (5) and these recordings are transmitted in digitized form to an evaluation unit (1). Finally, the discolourings, which occurred in the form of bands (6), are detected and at least partly quantified in the evaluation unit (1), such that a diagnosis suggestion is generated taking into account the number of bands (6) and the colour strength thereof. The described technical solution is distinguished by virtue of the camera (2) being used in each case to make at least two recordings at different times and/or under different recording conditions.

10 Claims, 1 Drawing Sheet

(51) Int. Cl.
  *G01N 21/25* (2006.01)
  *G01N 21/84* (2006.01)

(56) References Cited

U.S. PATENT DOCUMENTS

| | | | |
|---|---|---|---|
| 9,230,185 B1* | 1/2016 | Berry | G06K 9/36 |
| 2003/0139886 A1* | 7/2003 | Bodzin | G01N 21/47 |
| | | | 702/28 |
| 2003/0166019 A1* | 9/2003 | Wiltfang | C07K 16/18 |
| | | | 435/7.21 |
| 2005/0243321 A1* | 11/2005 | Cohen | G01N 33/521 |
| | | | 356/432 |
| 2008/0149855 A1 | 6/2008 | Mehta et al. | |
| 2013/0161190 A1* | 6/2013 | Ewart | G01N 27/27 |
| | | | 204/403.03 |
| 2013/0189794 A1* | 7/2013 | Emeric | B01L 3/50273 |
| | | | 436/501 |
| 2013/0267032 A1* | 10/2013 | Tsai | G06T 7/0012 |
| | | | 436/95 |
| 2014/0170757 A1* | 6/2014 | Tsai | G01N 21/78 |
| | | | 436/55 |

FOREIGN PATENT DOCUMENTS

| | | | | |
|---|---|---|---|---|
| WO | WO-2012131386 A1 * | 10/2012 | | G01N 21/8483 |
| WO | WO-2014113770 A1 * | 7/2014 | | A61B 5/0022 |
| WO | WO 2014/118151 A1 | 8/2014 | | |

OTHER PUBLICATIONS

Bio-Rad Laboratories, "Western Blotting Detection Reagents", Bulletin 2032 Rev F, Feb. 2011, retrieved from http://www.bio-rad.com/webroot/web/pdf/lsr/literature/Bulletin_2032F.pdf on Mar. 12, 2018, 10 pages.*
He et al. "Automated microfluidic protein immunoblotting" Nature Protocols vol. 5, pp. 1844-1856 (2010); doi:10.1038/nprot.2010. 142.*
Reinking, L. "ImageJ Basics", Biology 211 Laboratory Manual, Jun. 2007, retrieved from https://imagej.nih.gov/ij/docs/pdfs/ImageJ.pdf on Mar. 12, 2018, 3 pages.*
Color. (2016). In Editors of the American Heritage Dictionaries (Ed.), The American Heritage (R) dictionary of the English language (6th ed.). Boston, MA: Houghton Mifflin. Retrieved from https://search.credoreference.com/content/entry/hmdictenglang/color/0?institutionId=743, three pages.*
Definition of "discoloration", Oxford Dictionaries, retrieved from https://en.oxforddictionaries.com/definition/us/discoloration on Jun. 22, 2018, one page.*
Definition of "color", Oxford Dictionaries, retrieved from https://en.oxforddictionaries.com/definition/us/color on Jun. 22, 2018, five pages.*

"The Kodak Digital Science™ Image Station 440CF (IS440CF) system", retrieved from http://www.tau.ac.il/~zaslaysk/kodak.html on Mar. 12, 2018, one page/Dec. 2018, one page.*
Abouzied et al. "Simultaneous screening of fumonisin B1, aflatoxin B1, and zearalenone by line immunoblot: a computer-assisted multianalyte assay system" Journal of AOAC International vol. 77 (1994), pp. 495-501.*
Merriam-Webster Dictionary, definition for the term "bright", retrieved from https://www.merriam-webster.com/dictionary/bright on Nov. 4, 2019, 9 pages (Year: 2019).*
Merriam-Webster Dictionary, definition for the term "brightness", retrieved from https://www.merriam-webster.com/dictionary/brightness on Nov. 4, 2019, 7 pages (Year: 2019).*
Cadle et al. "Cellular Phone-Based Image Acquisition and Quantitative Ratiometric Method for Detecting Cocaine and Benzoylecgonine for Biological and Forensic Applications" Substance Abuse: Research and Treatment 2010:4 21-33 (Year: 2010).*
Carestream, "Carestream Gel Logic 2200 PRO User's Guide", IB5438234 Rev A Apr. 2010, retrieved from http://molecularbioimaging.com/files/77178679.pdf on Nov. 8, 2019, 152 pages (Year: 2010).*
Budowle et al. "Using a CCD Camera Imaging System as a Recording Device to Quantify Human DNA by Slot Blot Hybridization", BioTechniques vol. 30 (2001), 680-685 (Year: 2001).*
AlphaView Software User Guide, proteinsimple, P/N 94-13934-00 2011, 204 pages, retrieved from https://www.usf.edu/research-innovation/rf/usf-connect/documents/alphaview-user-guide.pdf (Year: 2011).*
LI-COR, Odyssey® Fc Application Protocols, Document No. 984-11166, Sep. 2011, 83 pages total.*
LI-COR, Odyssey® Fc Tutorial Manual, Version 1.0, Publication No. 984-11074, Jun. 2010, 48 pages total.*
Ornberg et al. "Western blot analysis with quantum dot fluorescence technology: a sensitive and quantitative method for multiplexed proteomics" Nature Methods 2:79-81, 2005.*
Combined Chinese Office Action and Search Report dated May 27, 2017 in Chinese Patent Application No. 201480023092.3 (with English language translation).
International Search Report dated Jul. 21, 2014 in PCT/EP2014/056787.
International Preliminary Report on Patentability and Written Opinion dated Oct. 27, 2015 in PCT/EP2014/056787 (with English language translation).
Yuzhi Chen, et al., "Amyloid precursor protein modulates beta-catenin degradation" Journal of Neuroinflammation, vol. 4, No. 1, XP021037916, Dec. 10, 2007, 10 Pages.
Hayeong Kwon, et al., "Caveolin-2 regulation of STAT3 transcriptional activation in response to insulin" Biochimica et Biophysica Acta, vol. 1793, No. 7, XP026684229, May 7, 2009, pp. 1325-1333.
S. Holmseth, et al., "The Concentrations and Distributions of Three C-Terminal Variants of the GLT1 (EAAT2; slc1a2) Glutamate Transporter Protein in Rate Brain Tissue Suggest Differential Regulation" Neuroscience, vol. 162, No. 4, XP026436784, Sep. 15, 2009, pp. 1055-1071.
C.D. Sladek, et al., "Characterization of Nuclear Neurokinin 3 Receptor Expression in Rat Brain" Neuroscience, vol. 196, XP028316200, Aug. 19, 2011, pp. 35-48.
Ahmed Elbaggari, et al., "Imaging of Chemiluminescent Western Blots: Comparison of Digital Imaging and X-ray Film" Bio-Rad Tech Note 5809, XP055125751, Jan. 1, 2008, 4 Pages.
Office Action dated Feb. 13, 2014 in German Patent Application No. 10 2013 008 468.7 (with unedited computer generated English translation).
Office Action dated Mar. 1, 2017 in European Patent Application No. 14 716 274.7 (with unedited computer generated English translation).
John F. Tarlton et al., "Clarification of immunoblots on polyvinylidene difluoride (PVDF) membranes for transmission densitometry", Journal of Immunological Methods, vol. 191, 1996, pp. 65-69.

\* cited by examiner

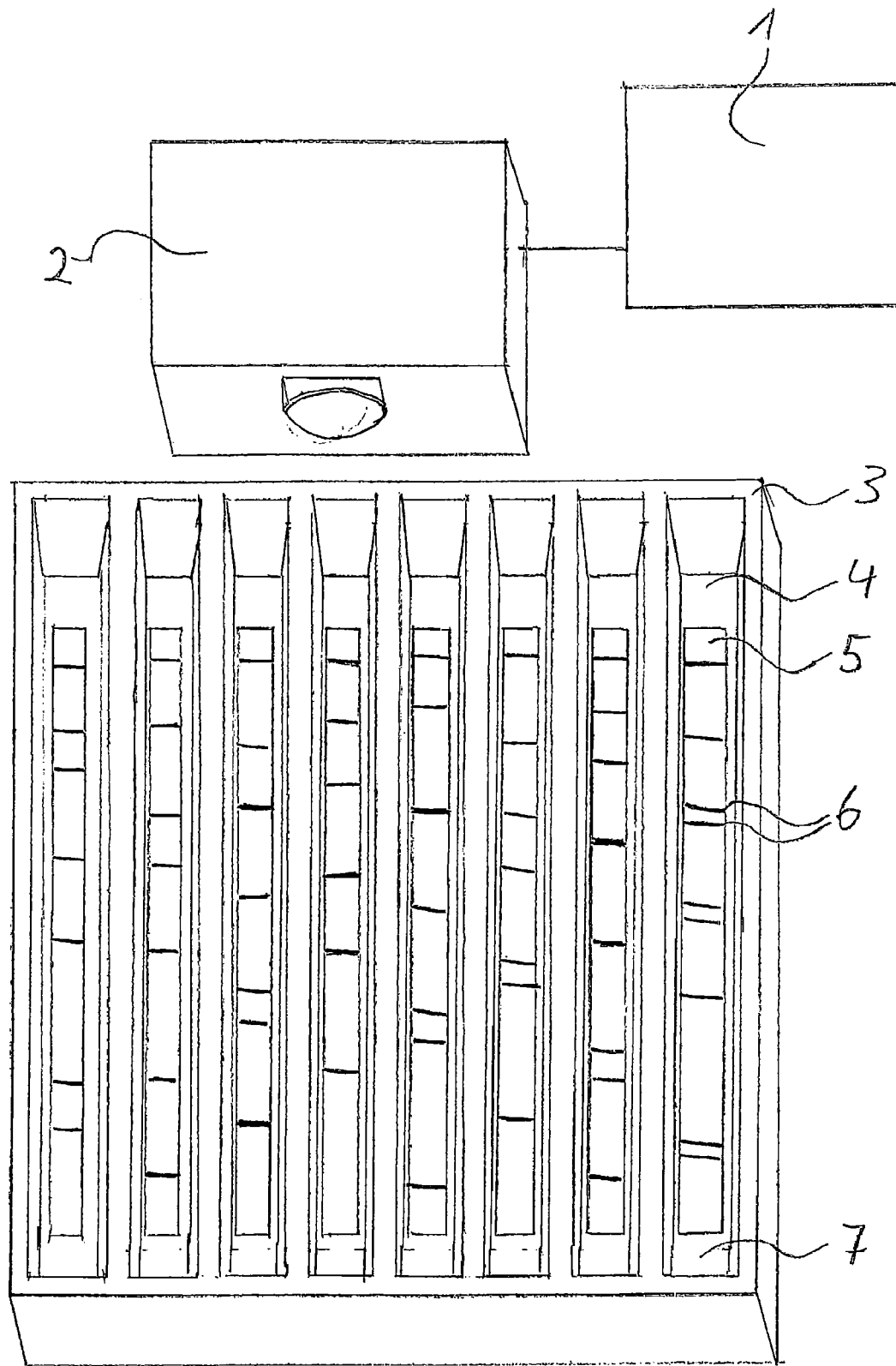

METHOD FOR AUTOMATED EVALUATION OF INCUBATED IMMUNOBLOT STRIPS

The invention relates to a device and a method for the automated evaluation of incubated immunoblot strips. What is essential to such immunoblot strips is that these have regions coated with antigens which, under the formation of so-called bands, discolor as soon as binding occurs, in particular between the antigen and an antibody present in a patient sample. Within the scope of the described technical solution, a camera is initially used to make records of the surfaces of at least two incubated immunoblot strips and these records are transmitted in digitized form to an evaluation unit. The discoloration that occurred in the form of bands is subsequently detected in the evaluation unit and at least partly quantified such that a diagnosis proposal is generated taking into account the number of bands and the color strength thereof.

Immunoblot strips, such as e.g. western blot strips or line blot strips are used in the field of in-vitro diagnostics to make a diagnosis in many cases. To this end, the immunoblot strips required in each case are inserted into incubation channels provided therefor, in which they are incubated with the required reagents and the patient sample. After a test is carried out correctly, specific discolorations, the so-called bands, appear on the immunoblot strips in the case of positively tested patient samples, as a result of which, in particular, binding of antibodies to the antigens provided on the immunoblot strips is detectable. The incubated immunoblot strips can either be evaluated by visual examination or the immunoblot strips are evaluated with the aid of automated or at least partly automated systems. In this context, the so-called EUROBlotCamera from EUROIMMUN Medizinische Labordiagnostika AG, which produces records of incubated immunoblot strips while the strips are still situated in the incubation channels in an incubation well, is known. The corresponding records are digitized, transmitted to a data evaluation unit and evaluated there with the aid of specific laboratory software. When evaluating the immunoblot strips, the occurrence of the bands and the discoloration of the individual bands compared to the background are established initially for preparing the creation of a diagnosis proposal. In the case of strong positive samples, there regularly is a strong discoloration on the immunoblot strips, while merely weak positive samples often only supply weak signals, which are therefore difficult to evaluate.

A similar system is known from WO99/53288, in which an automated system for evaluating borrelia blots is described. Here too, records of the incubated immunoblot strips are made with the aid of a digital camera and said records are transmitted to an electronic data processing unit for evaluation purposes. The discoloration of the bands in the case of positive patient samples is once again evaluated in a manner resolved according to color levels. A problem often occurring when using the described systems is that different membranes are used as a substrate for the production of immunoblot strips. In particular, use is made of membranes on the basis of PVDF, nylon or nitrocellulose. In relation to making records of the incubated immunoblot strips, what needs to be taken into account here is that the discoloration properties of the immunoblot strips made of different membranes often have significant differences, which may be problematic for an automated evaluation of the discoloration. Furthermore, the drying behavior of the aforementioned materials is different, and so records of immunoblot strips which have different amounts of residual moisture are sometimes made. The residual moisture in turn has a direct influence on the background color of an immunoblot strip and therefore on the establishment of the color difference between the band and background of the immunoblot strip. What should furthermore be taken into account is that even individual records of immunoblot strips with a set exposure time, with a defined illumination and/or according to set drying times do not always supply an ideal image in view of the background coloring or the conditions between band coloring and background coloring, or there may be an overexposure of the image, which ultimately leads to a more difficult image evaluation.

Proceeding from the known systems for automated evaluation of immunoblot strips and the aforementioned problems, the invention is based on the object of offering a system which renders possible a high quality evaluation of immunoblot strips, preferably even in the case where immunoblot strips made of different membranes are used or recorded simultaneously. Furthermore, the degree of residual moisture of different immunoblot strips should be unimportant so as to avoid it only being possible to carry out a high quality evaluation when all incubated immunoblot strips are at least almost dried. Furthermore, the technical solution according to the invention should ensure that the ratio between the discoloration of the individual bands and the background coloring, in particular, enables a reliable evaluation and that the risk of so-called overexposure can largely be precluded. The improved method and machine for carrying out this method should furthermore integrate easily into the known laboratory routine and be realized with comparatively simple means.

The problem described above is implemented with the aid of a method in accordance with claim 1 and a device according to claim 10, which is suitable for carrying out such a method. Advantageous embodiments of the invention are the subject matter of the dependent claims and are explained in more detail in the following description with partial reference to the FIGURES.

According to the invention, a method for the automated evaluation of incubated immunoblot strips, wherein a camera is used to take images, at least in regions, of a surface of an immunoblot strip which has antigens arranged thereon, in particular of the so-called discolored bands, and the images are transferred to an evaluation unit, in which a discoloration of the blot strip is detected in regions where antigens were applied and, on the basis of the detected discoloration, a diagnosis proposal is generated, was developed in such a way that the camera makes at least two records at different times and/or under different recording conditions.

In a preferred embodiment, the at least two records at different times comprise a first and a last record, and optionally additional records therebetween, wherein the time interval between the first and the last record is at least 0.5, 1, 2, 3, 4, 5, 7.5, 10, 12.5, 15, 20, 25, 30, 35, 40, 45, 50, 60, 80, 90, 100, 120, 150 or 180 minutes, more preferably at least 5, 10 or 15 minutes, most preferably at least 5 minutes.

Therefore, what is essential to the method according to the invention is that the conditions under which the individual records of the immunoblot strip are made vary and that, ultimately, the most suitable record is used for generating a diagnosis proposal. Thus, a virtual immunoblot strip is, as it were, composed from the most suitable images of the various records in a needs-oriented manner within the scope of the evaluation. The images of the discolored bands used for generating a diagnosis proposal can therefore originate from one record or from different records. Here, the change in the recording conditions can consist of various records being made at different times, in particular at different drying times, or else of records being made under different conditions.

A first, special embodiment of the invention provides for at least two records of the surface coated with antigens of at least one immunoblot strip being made, with the exposure times of the different records being different. Particularly preferably, at least two records are made of in each case at least two immunoblot strips.

The different records are transmitted to the evaluation unit in any case, within which evaluation unit the discoloration of the individual regions, the so-called bands, is compared to the background color of the respectively associated immunoblot strip and classified with the aid of a color scale which has integer values between 0 and 255. Initially, the different records are compared to one another in each case and the respective records of an immunoblot strip which have a particularly great color difference between the individual bands and the strip background are used to generate a diagnosis proposal. Bright records are used particularly preferably.

Therefore, the ideal records are filtered out from the various records in the evaluation unit in order to use these to generate the diagnosis proposal. In this context, it is conceivable for the ideal record of discoloration to be established either for each recorded strip or else for each test piece, in particular for line blots or membrane chips with individual test pieces arranged thereon. Therefore, the bands of the strip best suitable for the evaluation are always filtered out initially and these bands are taken into account for the automated generation of a diagnosis proposal. In this context, provision is made for the individual records of the bands of an immunoblot strip to be compared and for respectively the best record of a band to be used to generate a diagnosis proposal. In accordance with this embodiment, it is conceivable that an as it were virtual immunoblot strip is taken into account when generating a diagnosis proposal, which virtual immunoblot strip is composed of records of bands which were recorded at different times and/or under different recording conditions, in particular with different exposure time and/or varying brightness. With the aid of this measure, it is thus possible to generate a multiplicity of records at different times and/or under different conditions and to use the respective best record to generate a diagnosis proposal. Hence, the quality when generating a diagnosis proposal is increased significantly.

Alternatively, or in addition to the variation of the exposure time of at least two records, it is likewise conceivable to make various records at different brightness levels or using a different type of illumination for the immunoblot strip. The essential concept in this case is also that of generating a plurality of records and of ultimately using the most suitable record for the evaluation, with optionally different bands from different records also being taken into account.

In a preferred embodiment, the brightness, preferably expressed as illuminance, differs between the record with the highest brightness and the record with the lowest brightness among the at least two records by at least 5%, 10%, 15%, 20%, 25%, 30%, 40%, 50% 60%, 70%, 80%, 90%, 100%, 125%, 150%, 175% or 200% of the brightness of the record with the lowest brightness.

In accordance with a special development, the at least two records are recorded at exposure times of between and 50 ms. It is particularly advantageous if at least five records of the at least two incubated immunoblot strips are initially made for the automated generation of a diagnosis proposal.

In this context, it is once again feasible for the exposure times of the individual records to differ, with, preferably, exposure times of 21, 28, 35, 42 and 49 ms being selected in the case of five records. In contrast to the known systems, in which the discoloration of a band is preferably classified under averaging in the case of an average exposure time, it is possible in accordance with the method according to the invention to seek out the most suitable record for the evaluation from the different records that were made with different exposure times.

In this context, it is explicitly mentioned that the method according to the invention is particularly well-suited to the evaluation of immunoblot strips, in particular western blot strips or line blot strips, but that, moreover, it is likewise feasible to evaluate other substrates, such as e.g. object carriers or biochips, onto which membranes coated with antigens are applied, using the method according to the invention.

Moreover, the invention relates to a device that is suitable for carrying out the method according to the invention, which is based on performing a plurality of recordings at different times and/or in different recording conditions in order to evaluate incubated immunoblot strips. Such a device essentially comprises a digital camera or a CCD sensor, which makes records of incubated immunoblot strips. The immunoblot strip or strips is/are preferably still situated in the incubation channels of an incubation well during the recordings. The digitized records are fed to an evaluation unit, in which the record in which the individual bands have the greatest color difference in relation to the background or the background color is chosen from the different records. In this case, it is once again feasible either to select those individual images of the discolored surface regions, i.e. the bands, which, when considered over all bands, enable the best evaluation or else to combine the highest contrast bands of the different strips together for evaluation purposes.

Below, with the aid of the FIGURE, the invention is explained in more detail on the basis of an exemplary embodiment, without loss of the general inventive concept. In detail:

FIGURE: shows an incubation well with a multiplicity of incubation channels, in which incubated immunoblot strips are situated and recorded with the aid of a digital camera.

The FIGURE shows a camera 2 arranged above an incubation well 3 having a multiplicity of incubation channels 4, which camera makes records of immunoblot strips 5 situated in the channels 4 and transfers these in digitized form to an evaluation unit 1. The immunoblot strips 5 arranged in the individual channels were already incubated and are already at least partly dried. It can clearly be identified that the various immunoblot strips 5 have discoloration in the form of bands 6 at different positions. Antigens which exhibit a positive reaction with antibodies of an examined patient sample are situated at these positions on the surfaces of the test strips 5. Thus, it is possible to generate a diagnosis proposal, which provides information about how high the probability is that a patient has fallen ill with a specific disease. Reference is explicitly made to the fact that it is irrelevant to the described device and the performed method as to whether only one incubation channel is filled with a blot strip or whether blot strips are situated in at least two channels. It is conventional, already for work-economical and economical aspects, to equip a plurality of channels of an incubation well with immunoblot strips and to incubate these simultaneously and evaluate these subsequently.

The evaluation of incubated immunoblot strips 5 is implemented in an automated manner with the aid of a digital camera 2. The digital camera 2 successively makes a total of five records of the surfaces of the immunoblot strips 5 situated in the channels 4, which records differ in relation to the exposure time. Records are created with an exposure time of 21, 28, 35, 42 and 49 ms. Therefore, finally, five digitized records of each incubated immunoblot strip 5 situated in an incubation channel 4 are transmitted to the evaluation unit 1. Initially, the discoloration of the individual bands compared to the discoloration of the background 7 is established in the evaluation unit 1 for the various records and each of these band discolorations is assigned a numerical value representing the respective color level, said numerical value being integer and lying between 0 and 255.

The bands 6 of the individual immunoblot strips 5 which show the clearest discoloration compared to the background 7 are selected in the next step. The best records, namely the records having the clearest color difference of a band 6 in relation to the respective background 7, are finally selected in relation to an immunoblot strip 5, with it being possible for the various selected records to have been recorded at different times and, in this case, with different exposure times. The records of the band discolorations filtered out as ideal records are finally evaluated with the aid of electronic laboratory software and hence a diagnosis proposal is generated. As a result of the described method, it is possible to establish the ideal record for each individual strip or even, particularly when using line blots with individually applied, antigen-carrying membrane chips, filter out the respectively ideal records of the individual membrane chips and use this, as it were as an optimized overall image of an incubated immunoblot strip, to generate a diagnosis proposal.

LIST OF REFERENCE SIGNS

1 Evaluation unit
2 Camera
3 Incubation well
4 Incubation channel
5 Incubated immunoblot strip
6 Band
7 Background

The invention claimed is:

1. A method for the automated evaluation of an incubated immunoblot strip, comprising:
 taking, with a camera, at least two images of at least a portion of said immunoblot strip, wherein the at least a portion of the immunoblot strip comprises at least two test bands and a background, each of the at least two test bands comprising a region of the immunoblot strip with an antigen applied thereon and the background comprising a portion of the immunoblot strip without an antigen applied thereon, wherein the at least two images are taken under different exposure times and/or recording conditions, and wherein each of the at least two images displays discoloration of the at least two test bands;
 detecting the discoloration of the immunoblot strip in said region for each of the at least two test bands in each of the at least two images;
 comparing each of the at least two images to a background color of the immunoblot strip, the background color corresponding to the background of the immunoblot strip;
 for each of the at least two test bands, selecting one of the at least two images that has a largest color difference in relation to the background color, wherein a first of the at least two images is selected for a first of the at least two test bands and a second of the at least two images is selected for a second of the at least two test bands; and
 combining the first of the at least two images and the second of the at least two images to generate a virtual immunoblot strip such that a best record, corresponding to the largest color difference for each of the at least two test bands, forms an overall image of the incubated immunoblot strip,
 wherein the at least two images are recorded with different exposure times, or wherein the at least two images are recorded at different brightness levels.

2. The method as claimed in claim 1, wherein five images are recorded with different exposure times.

3. The method as claimed in claim 1, wherein the at least two images are recorded at exposure times of between 20 and 50 ms.

4. The method according to claim 1, wherein the color difference is classified in integer levels between 0 and 255.

5. The method as claimed in claim 1, wherein said at least two images are recorded at different times and under different exposure times.

6. A method for the automated evaluation of a plurality of incubated immunoblot strips, comprising:
 taking, with a camera, at least two images of at least a portion of said plurality of incubated immunoblot strips, wherein the at least a portion of the plurality of incubated immunoblot strips comprises at least two test bands and a background, each of the at least two test bands comprising a region of the plurality of incubated immunoblot strips with an antigen applied thereon and the background comprising a portion of the plurality of incubated immunoblot strips without an antigen applied thereon, wherein the at least two images are taken under different exposure times and/or recording conditions, and wherein each of the at least two images displays discoloration of the at least two test bands; and
 detecting the discoloration of the plurality of incubated immunoblot strips in said region for each of the at least two test bands in each of the at least two images;
 comparing each of the at least two images to a background color of each of the plurality of incubated immunoblot strips, the background color corresponding to the background of each of the plurality of incubated immunoblot strips;
 for each of the at least two test bands, selecting one of the at least two images that has a largest color difference in relation to the background color, wherein a first of the at least two images is selected for a first test band for a first of the plurality of incubated immunoblot strips and a second of the at least two images is selected for a second test band for a second of the plurality of incubated immunoblot strips; and
 combining the first of the at least two images and the second of the at least two images to generate a virtual immunoblot strip for each of the plurality of incubated immunoblot strips such that a best record, corresponding to the largest color difference for each test band, forms an overall image of each of the plurality of incubated immunoblot strips,
 wherein the at least two images are recorded with different exposure times or wherein the at least two images are recorded at different brightness levels.

7. The method as claimed in claim 6, wherein five images are recorded with different exposure times.

8. The method as claimed in claim 6, wherein the at least two images are recorded at exposure times of between 20 and 50 ms.

9. The method according to claim 6, wherein the color difference is classified in integer levels between 0 and 255.

10. The method as claimed in claim 6, wherein said at least two images are recorded at different times and under different exposure times.

* * * * *